US008744555B2

(12) United States Patent
Allavatam et al.

(10) Patent No.: US 8,744,555 B2
(45) Date of Patent: Jun. 3, 2014

(54) ADAPTIVE WAVEFORM APPRAISAL IN AN IMPLANTABLE CARDIAC SYSTEM

(75) Inventors: Venugopal Allavatam, Oceanside, CA (US); Rick Sanghera, San Clemente, CA (US); Jay A. Warren, San Juan Capistrano, CA (US)

(73) Assignee: Cameron Health, Inc., San Clemente, CA (US)

( * ) Notice: Subject to any disclaimer, the term of this patent is extended or adjusted under 35 U.S.C. 154(b) by 520 days.

(21) Appl. No.: 12/913,647

(22) Filed: Oct. 27, 2010

(65) Prior Publication Data

US 2011/0098775 A1    Apr. 28, 2011

Related U.S. Application Data

(60) Provisional application No. 61/255,253, filed on Oct. 27, 2009.

(51) Int. Cl.
*A61B 5/04* (2006.01)
*A61B 5/02* (2006.01)

(52) U.S. Cl.
USPC ............................ 600/509; 600/508; 600/513

(58) Field of Classification Search
USPC .......................................... 600/508–509, 513
See application file for complete search history.

(56) References Cited

U.S. PATENT DOCUMENTS

| | | | |
|---|---|---|---|
| 4,184,493 A | 1/1980 | Langer et al. | |
| 4,300,567 A | 11/1981 | Kolenik et al. | |
| 4,407,288 A | 10/1983 | Langer et al. | |
| 4,450,527 A | 5/1984 | Sramek | |
| 4,457,315 A | 7/1984 | Bennish | |
| 4,595,009 A | 6/1986 | Leinders | |
| 4,679,144 A | 7/1987 | Cox et al. | |
| 4,693,253 A | 9/1987 | Adams | |
| 4,750,494 A | 6/1988 | King | |
| 4,779,617 A | 10/1988 | Whigham | |
| 4,979,110 A | 12/1990 | Albrecht et al. | |
| 4,989,602 A | 2/1991 | Sholder et al. | |
| 5,000,189 A | 3/1991 | Throne et al. | |
| 5,105,810 A | 4/1992 | Collins et al. | |

(Continued)

FOREIGN PATENT DOCUMENTS

EP     0554208 A2     8/1993

OTHER PUBLICATIONS

Gunderson et al., "An Algorithm to Predict Implantable Cardioverter-Defibrillator Lead Failure," JACC, Nov. 2004, vol. 44, No. 9, pp. 1898-1902.

(Continued)

*Primary Examiner* — Nicole F Lavert
(74) *Attorney, Agent, or Firm* — Schwegman, Lundberg & Woessner, P.A.

(57) ABSTRACT

Methods and implantable devices for cardiac signal analysis. The methods and devices make use of waveform appraisal techniques to distinguish event detections into categories for suspect events and waveform appraisal passing events. When adjustments are made to the data entering analysis for waveform appraisal, the waveform appraisal thresholds applied are modified as well. For example, when the data analysis window for waveform appraisal changes in length, a waveform appraisal threshold is modified. Other changes, including changes in sensing characteristics with which waveform appraisal operates may also result in changes to the waveform appraisal threshold including changes in gain, sensing vector, activation of other devices, implantee posture and other examples which are explained.

20 Claims, 8 Drawing Sheets

(56) References Cited

U.S. PATENT DOCUMENTS

| | | |
|---|---|---|
| 5,184,616 A | 2/1993 | Weiss |
| 5,193,535 A | 3/1993 | Bardy et al. |
| 5,215,098 A | 6/1993 | Steinhaus et al. |
| 5,217,021 A | 6/1993 | Steinhaus et al. |
| 5,271,411 A | 12/1993 | Ripley et al. |
| 5,280,792 A | 1/1994 | Leong et al. |
| 5,299,119 A | 3/1994 | Kraf et al. |
| 5,313,953 A | 5/1994 | Yomtov et al. |
| 5,331,966 A | 7/1994 | Bennett et al. |
| 5,342,402 A | 8/1994 | Olson et al. |
| 5,342,407 A | 8/1994 | Dahl et al. |
| 5,351,696 A | 10/1994 | Riff et al. |
| 5,376,104 A | 12/1994 | Sakai et al. |
| 5,423,326 A | 6/1995 | Wang et al. |
| 5,447,519 A | 1/1996 | Kim et al. |
| 5,522,852 A | 6/1996 | White et al. |
| 5,534,019 A | 7/1996 | Paspa |
| 5,545,186 A | 8/1996 | Olson et al. |
| 5,558,098 A | 9/1996 | Fain |
| 5,607,455 A | 3/1997 | Armstrong |
| 5,658,317 A | 8/1997 | Haefner et al. |
| 5,709,215 A | 1/1998 | Perttu et al. |
| 5,817,134 A | 10/1998 | Greenhut et al. |
| 5,827,197 A | 10/1998 | Bocek et al. |
| 5,857,977 A | 1/1999 | Caswell et al. |
| 5,991,657 A | 11/1999 | Kim |
| 6,041,251 A | 3/2000 | Kim et al. |
| 6,047,210 A | 4/2000 | Kim et al. |
| 6,052,617 A | 4/2000 | Kim |
| 6,058,328 A | 5/2000 | Levine et al. |
| 6,095,987 A | 8/2000 | Shmulewitz et al. |
| 6,115,628 A | 9/2000 | Stadler et al. |
| 6,144,879 A | 11/2000 | Gray |
| 6,148,230 A | 11/2000 | KenKnight |
| 6,223,078 B1 | 4/2001 | Marcovecchio |
| 6,230,055 B1 | 5/2001 | Sun et al. |
| 6,236,882 B1 | 5/2001 | Lee et al. |
| 6,240,313 B1 | 5/2001 | Esler |
| 6,266,554 B1 | 7/2001 | Hsu et al. |
| 6,280,462 B1 | 8/2001 | Hauser et al. |
| 6,308,095 B1 | 10/2001 | Hsu et al. |
| 6,334,071 B1 | 12/2001 | Lu |
| 6,377,844 B1 | 4/2002 | Graen |
| 6,381,493 B1 | 4/2002 | Stadler et al. |
| 6,393,316 B1 | 5/2002 | Gillberg et al. |
| 6,397,100 B2 | 5/2002 | Stadler et al. |
| 6,411,844 B1 | 6/2002 | Kroll et al. |
| 6,438,410 B2 | 8/2002 | Hsu et al. |
| 6,449,503 B1 | 9/2002 | Hsu |
| 6,493,579 B1 | 12/2002 | Gilkerson et al. |
| 6,493,584 B1 | 12/2002 | Lu |
| 6,505,068 B2 | 1/2003 | Bonnet et al. |
| 6,516,225 B1 | 2/2003 | Florio |
| 6,561,984 B1 | 5/2003 | Turcott |
| 6,567,691 B1 | 5/2003 | Stadler |
| 6,574,505 B1 | 6/2003 | Warren |
| 6,575,912 B1 | 6/2003 | Turcott |
| 6,587,720 B2 | 7/2003 | Hsu et al. |
| 6,625,490 B1 | 9/2003 | McClure et al. |
| 6,643,549 B1 | 11/2003 | Bradley et al. |
| 6,647,292 B1 | 11/2003 | Bardy et al. |
| 6,684,100 B1 | 1/2004 | Sweeney et al. |
| 6,699,200 B2 | 3/2004 | Cao et al. |
| 6,708,058 B2 | 3/2004 | Kim et al. |
| 6,708,062 B2 | 3/2004 | Ericksen et al. |
| 6,721,597 B1 | 4/2004 | Bardy et al. |
| 6,728,572 B2 | 4/2004 | Hsu et al. |
| 6,731,978 B2 | 5/2004 | Olson et al. |
| 6,745,068 B2 | 6/2004 | Koyrakh et al. |
| 6,754,528 B2 | 6/2004 | Bardy et al. |
| 6,889,079 B2 | 5/2005 | Bocek et al. |
| 6,909,916 B2 | 6/2005 | Spinelli et al. |
| 6,950,702 B2 | 9/2005 | Sweeney |
| 7,016,730 B2 | 3/2006 | Ternes |
| 7,020,523 B1 | 3/2006 | Lu et al. |
| 7,027,856 B2 | 4/2006 | Zhou et al. |
| 7,027,858 B2 | 4/2006 | Cao et al. |
| 7,027,862 B2 | 4/2006 | Dahl et al. |
| 7,031,764 B2 | 4/2006 | Schwartz et al. |
| 7,062,314 B2 | 6/2006 | Zhu et al. |
| 7,062,315 B2 | 6/2006 | Koyrakh et al. |
| 7,062,322 B2 | 6/2006 | Stadler et al. |
| 7,076,289 B2 | 7/2006 | Sarkar et al. |
| 7,085,599 B2 | 8/2006 | Kim et al. |
| 7,117,035 B2 | 10/2006 | Wagner et al. |
| 7,149,575 B2 | 12/2006 | Ostroff et al. |
| 7,162,301 B2 | 1/2007 | Kim et al. |
| 7,167,747 B2 | 1/2007 | Gunderson et al. |
| 7,184,815 B2 | 2/2007 | Kim et al. |
| 7,184,818 B2 | 2/2007 | Kim et al. |
| 7,191,004 B2 | 3/2007 | Kim et al. |
| 7,194,302 B2 | 3/2007 | Bardy et al. |
| 7,218,966 B2 | 5/2007 | Haefner |
| 7,236,819 B2 | 6/2007 | Brockway et al. |
| 7,248,921 B2 | 7/2007 | Palreddy et al. |
| 7,266,409 B2 | 9/2007 | Gunderson |
| 7,283,863 B2 | 10/2007 | Gunderson |
| 7,302,294 B2 | 11/2007 | Kamath et al. |
| 7,330,757 B2 | 2/2008 | Ostroff et al. |
| 7,346,392 B2 | 3/2008 | KenKnight |
| 7,376,458 B2 | 5/2008 | Palreddy et al. |
| 7,379,772 B2 | 5/2008 | Bardy et al. |
| 7,386,342 B1 | 6/2008 | Falkenberg et al. |
| 7,392,085 B2 | 6/2008 | Warren et al. |
| 7,444,182 B2 | 10/2008 | Ostroff et al. |
| 7,447,540 B1 | 11/2008 | Nabutovsky et al. |
| 7,467,009 B2 | 12/2008 | Palreddy et al. |
| 7,477,935 B2 | 1/2009 | Palreddy et al. |
| 7,496,408 B2 | 2/2009 | Ghanem et al. |
| 7,496,409 B2 | 2/2009 | Greenhut et al. |
| 7,499,750 B2 | 3/2009 | Haefner et al. |
| 7,522,959 B2 | 4/2009 | Hauser et al. |
| 7,546,159 B1 | 6/2009 | Nabutovsky et al. |
| 7,555,335 B2 | 6/2009 | Kamath et al. |
| 7,559,900 B2 | 7/2009 | Gillberg |
| 7,567,835 B2 | 7/2009 | Gunderson et al. |
| 7,570,997 B2 | 8/2009 | Lovett et al. |
| 7,593,771 B2 | 9/2009 | Yonce et al. |
| 7,623,913 B2 | 11/2009 | Phillips |
| 7,623,916 B2 | 11/2009 | Julian |
| 7,655,014 B2 | 2/2010 | Ko et al. |
| 7,682,316 B2 | 3/2010 | Anderson et al. |
| 7,684,864 B2 | 3/2010 | Olson et al. |
| 7,715,906 B2 | 5/2010 | Krause et al. |
| 7,734,345 B2 | 6/2010 | Cinbis |
| 7,761,142 B2 | 7/2010 | Ghanem et al. |
| 7,774,049 B2 | 8/2010 | Ghanem et al. |
| 7,783,354 B2 | 8/2010 | Gunderson |
| 7,797,036 B2 | 9/2010 | Zhang et al. |
| 7,865,233 B2 | 1/2011 | Haefner |
| 7,894,894 B2 | 2/2011 | Stadler et al. |
| 7,904,142 B2 | 3/2011 | Kim et al. |
| 7,904,153 B2 | 3/2011 | Greenhut et al. |
| 7,907,993 B2 | 3/2011 | Ghanem et al. |
| 2004/0215239 A1 | 10/2004 | Favet et al. |
| 2004/0215240 A1 | 10/2004 | Lovett et al. |
| 2004/0220628 A1 | 11/2004 | Wagner |
| 2004/0230229 A1 | 11/2004 | Lovett et al. |
| 2005/0107838 A1 | 5/2005 | Lovett et al. |
| 2005/0131464 A1 | 6/2005 | Heinrich et al. |
| 2005/0154421 A1 | 7/2005 | Ousdigian |
| 2006/0167502 A1 | 7/2006 | Haefner |
| 2006/0167503 A1 | 7/2006 | Warren et al. |
| 2006/0167504 A1 | 7/2006 | Warren et al. |
| 2006/0241701 A1 | 10/2006 | Markowitz et al. |
| 2007/0032829 A1 | 2/2007 | Ostroff |
| 2007/0049975 A1 | 3/2007 | Cates et al. |
| 2007/0135847 A1 | 6/2007 | Kenknight |
| 2007/0142736 A1 | 6/2007 | Cazares et al. |
| 2007/0156190 A1 | 7/2007 | Cinbis et al. |
| 2007/0179539 A1 | 8/2007 | Degroot et al. |
| 2007/0179540 A1 | 8/2007 | Stegemann et al. |
| 2007/0232944 A1 | 10/2007 | Ghanem et al. |
| 2007/0232945 A1 | 10/2007 | Kleckner et al. |

(56) References Cited

U.S. PATENT DOCUMENTS

| | | |
|---|---|---|
| 2007/0232948 A1 | 10/2007 | Stadler et al. |
| 2007/0233198 A1 | 10/2007 | Ghanem et al. |
| 2007/0276445 A1 | 11/2007 | Sanghera et al. |
| 2008/0015647 A1 | 1/2008 | Palreddy et al. |
| 2008/0061961 A1* | 3/2008 | John .................. 340/539.12 |
| 2008/0077030 A1 | 3/2008 | Ostroff et al. |
| 2008/0086174 A1 | 4/2008 | Libbus et al. |
| 2008/0091242 A1 | 4/2008 | Kamath et al. |
| 2008/0132965 A1 | 6/2008 | Ostroff et al. |
| 2008/0161870 A1 | 7/2008 | Gunderson |
| 2008/0172098 A1 | 7/2008 | Gunderson |
| 2008/0183085 A1 | 7/2008 | Van Oort et al. |
| 2008/0188901 A1 | 8/2008 | Sanghera et al. |
| 2008/0215110 A1 | 9/2008 | Gunderson |
| 2008/0221632 A1 | 9/2008 | Bardy et al. |
| 2008/0228093 A1 | 9/2008 | Dong et al. |
| 2008/0243200 A1 | 10/2008 | Scinicariello et al. |
| 2008/0262559 A1 | 10/2008 | Zhang et al. |
| 2008/0275516 A1 | 11/2008 | Ghanem et al. |
| 2008/0275517 A1 | 11/2008 | Ghanem et al. |
| 2008/0275519 A1 | 11/2008 | Ghanem et al. |
| 2008/0275521 A1 | 11/2008 | Warren et al. |
| 2009/0036788 A1 | 2/2009 | Nabutovsky et al. |
| 2009/0043352 A1 | 2/2009 | Brooke et al. |
| 2009/0054796 A1 | 2/2009 | Marcovecchio et al. |
| 2009/0054938 A1 | 2/2009 | Ostroff et al. |
| 2009/0093731 A1 | 4/2009 | Palreddy et al. |
| 2009/0156957 A1 | 6/2009 | Linder et al. |
| 2009/0157128 A1 | 6/2009 | Seim et al. |
| 2009/0157132 A1 | 6/2009 | Linder et al. |
| 2009/0157137 A1 | 6/2009 | Gilkerson et al. |
| 2009/0240157 A1 | 9/2009 | Liam et al. |
| 2009/0240300 A1 | 9/2009 | Liam et al. |

OTHER PUBLICATIONS

Olson et al., "Onset and Stability for Ventricular Tachyarrhythmia Detection in an Implantable Pacer-Cardioverter-Defibrillator," IEEE, (1987) pp. 167-170.

Schuder, "The Role of an Engineering Oriented Medical Research Group in Developing Improved Methods and Devices for Achieving Ventricular Defibrillation: The University of Missouri Experience," PACE, vol. 16, Jan. 1993, pp. 95-124.

Schwake et al., "Komplikationen nit Sonden bei 340 Patienten mit einem Implantierbaren Kardioverter/Defibrillator," Z Kardiol (1999)vol. 88, No. 8 pp. 559-565.

Swerdlow, et al., "Advanced ICD Troubleshooting: Part I," online article at http://www.medscape.com/viewarticle/520588_print, accessed and printed Jul. 7, 2009, indicates publication Jan. 9, 2006 (publication date not confirmed).

Throne, "A Comparison of Four New Time-Domain Techniques for Discriminating Monomorphic Ventricular Tachycardia from Sinus Rhythm Using Ventricular Waveform Morphology," IEEE Transactions on Biomedical Engineering, vol. 38, No. 6, Jun. 1991, pp. 561-570.

* cited by examiner

ADAPTIVE WAVEFORM APPRAISAL IN AN IMPLANTABLE CARDIAC SYSTEM

RELATED APPLICATIONS

The present application claims the benefits of and priority to U.S. Provisional Patent Application No. 61/255,253, titled ADAPTIVE WAVEFORM APPRAISAL IN AN IMPLANTABLE CARDIAC SYSTEM, filed 27 Oct. 2009, the entire disclosure of which is incorporated herein by reference.

FIELD

The present invention relates generally to implantable medical device systems that sense and analyze cardiac signals. More particularly, the present invention relates to implantable medical devices that sense cardiac signals within an implantee's body in order to classify cardiac activity as likely benign or malignant.

BACKGROUND

An implantable cardiac stimulus device (ICSD) typically senses cardiac electrical signals in an implantee and uses the sensed signals to classify the implantee's cardiac rhythm as normal/benign or malignant/treatable. Illustrative malignant arrhythmias may include ventricular fibrillation and/or ventricular tachyarrhythmia. Other conditions including non-ventricular arrhythmias may also be considered "treatable" depending upon patient characteristics and physician preferences.

A method of analyzing cardiac signal data may begin by detecting cardiac events in sensed signals. However, signals sensed by implantable cardiac systems can be subjected to many sources of noise, where noise, for a cardiac system, is defined as any non-cardiac signal. Differentiating noise from likely cardiac events can be a challenging task for the implantable device.

New or alternative methods for ensuring accurate cardiac event detection are desired.

SUMMARY

In a first illustrative embodiment, an implantable cardiac system uses a set of noise analysis rules to differentiate noise from cardiac events and dynamically adapts the rules in response to sensing/detection parameters or identified signal/rhythm characteristics. In one embodiment, an analysis window is defined for detected events, and the length of the analysis window is modified in response to changing detected event rate, thus changing a sensing parameter in view of detected conditions. Modification may be accomplished via external programmer or by the device's own dynamic analysis. When the sensing parameter (the analysis window length) changes, the method responds by changing the noise analysis rules. Implantable devices and implantable device systems configured to perform or use like methods make up additional embodiments.

DETAILED DESCRIPTION

The following detailed description should be read with reference to the drawings. The drawings, which are not necessarily to scale, depict illustrative embodiments and are not intended to limit the scope of the invention. Some of the following examples and explanations include references to issued patents and pending patent applications. These references are for illustrative purposes and are not intended to limit the use of other methods or devices.

Several embodiments disclosed herein can be used in an implantable cardiac stimulus device (ICSD). One type of ICSD is an implantable cardioverter-defibrillator, which can provide therapy in the form of cardioversion and/or defibrillation therapies and, when needed/programmed, anti-bradycardia pacing. An ICSD may instead or in addition provide anti-tachycardia pacing, for example in a tiered therapy system, and/or other pacing therapies, such as bradycardia pacing, or any other suitable therapy. Other devices, including implantable and/or external monitoring or therapy devices directed at cardiac or non-cardiac conditions or sensing may also serve as embodiments.

Figure 1:
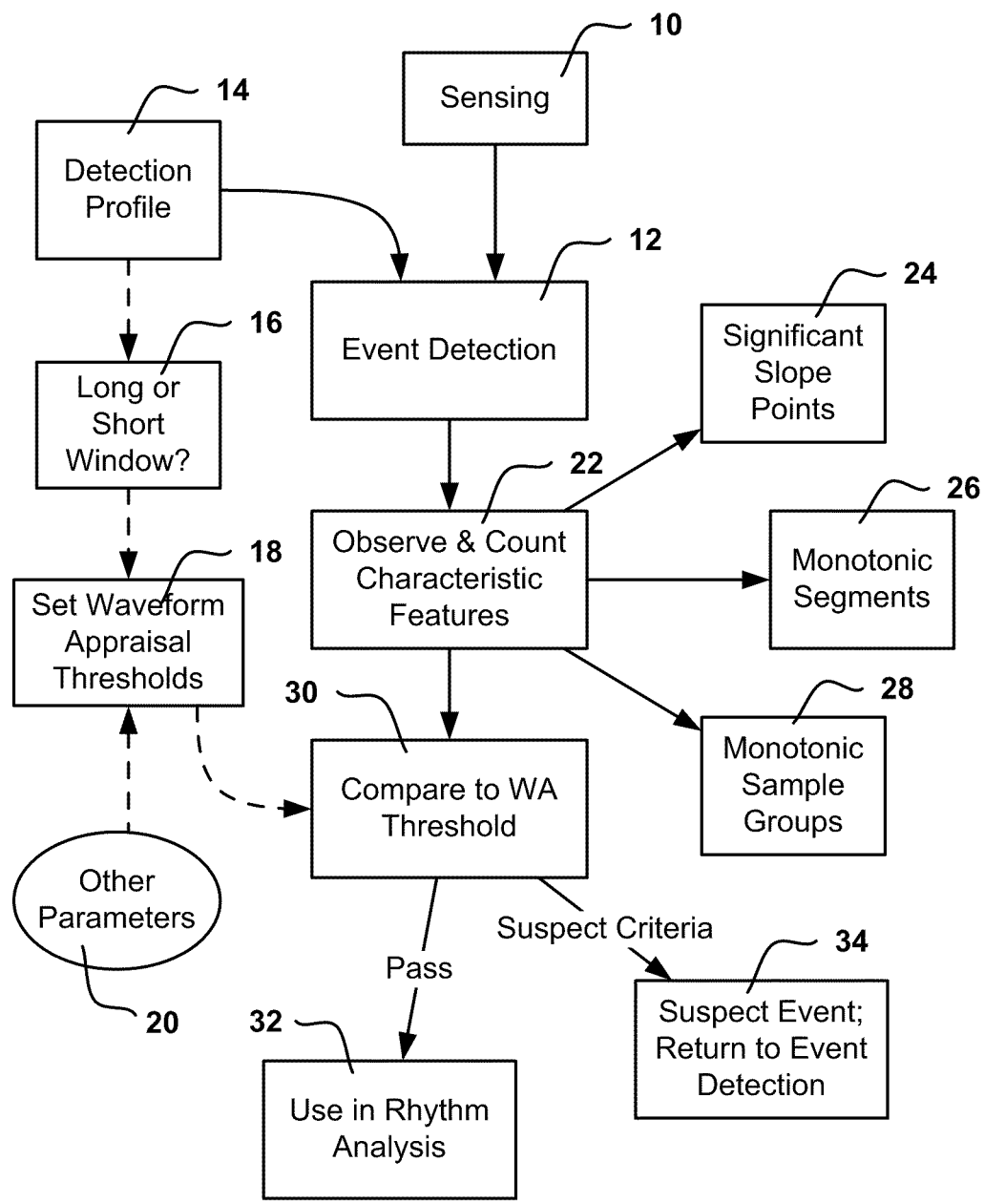
FIG. 1 shows, in block form, an illustrative method for managing event detection.

FIG. 1 shows, in block form, an illustrative method for managing event detection. The method is designed to apply a set of waveform appraisal rules to identify and mark noisy detected events as suspect events. After waveform appraisal, detected events that are not identified as noisy are treated as "passing" waveform appraisal. As used herein, "noise" is a signal originating outside of the intended signal source, for example, for an ICSD, noise may be defined as any signal having a non-cardiac source. For non-cardiac devices, the term "noise" may refer to any signal generated by a source other than a target source; for example, if the target source is a patient's diaphragm, then signals from anything other than the diaphragm may be treated as noise. Other definitions of noise may apply.

In the illustrative method, sensing block 10 represents the activity of receiving or capturing signals. For example, an implanted system would sense signals from implanted electrodes. Other signal inputs may be used for example via interrogation of remote passive devices, and/or signals that may be received via telemetry. In the example shown, events are detected at block 12 from the sensed signals. Event detection 12 may use a detection profile 14, where the detection profile gives parameters defining a detection threshold. When the sensed signal crosses the detection threshold, a detected event (or detection) is declared at block 12. In this example, the parameters of the detection profile 14 are reviewed to determine whether a long or short window for waveform appraisal analysis is defined, as noted at block 16, and then waveform appraisal thresholds are defined as shown at 18. Other parameters of sensing or detection may also inform the setting of waveform appraisal thresholds, as noted at 20 (some illustrative "other parameters" are further explained below).

The waveform appraisal includes observing and counting characteristic features 22 of the detected event. Some characteristic features that may be observed include significant slope points 24 (an example is shown below in FIG. 5A); monotonic segments 26 (an example is shown below in FIG. 5B); and monotonic sample groups 28 (an example is shown below in FIG. 5C). The counting of characteristic features in block 22 is performed within a waveform appraisal window, the same window used in block 16 to construct waveform appraisal thresholds 18.

Next, the counted observed characteristic features from block 22 are compared to the waveform appraisal thresholds set in block 18 at comparison 30. This comparison results in the detected event passing and being used in further analysis, such as rhythm analysis 32, or in the detected event meeting suspect criteria and being marked as a suspect event, as noted at block 34. If the detected event is marked as a suspect event, then data for the suspect event itself, such as shape or timing data, is not passed to further analysis which may include, for example, rate and/or rhythm analysis, and the system returns to sensing 10 and event detection 12 to wait for a next detection.

Certain details of methods for use in block 22, along with blocks 24, 26, and 28, are further described in U.S. Pat. No. 7,248,921, titled METHOD AND DEVICES FOR PERFORMING CARDIAC WAVEFORM APPRAISAL. The difference in FIG. 1, as further highlighted below, is that the detection profile settings 14 and/or other parameters 20 are used to dynamically change the waveform appraisal thresholds that are set at block 18 and then used in block 22.

Figure 2:
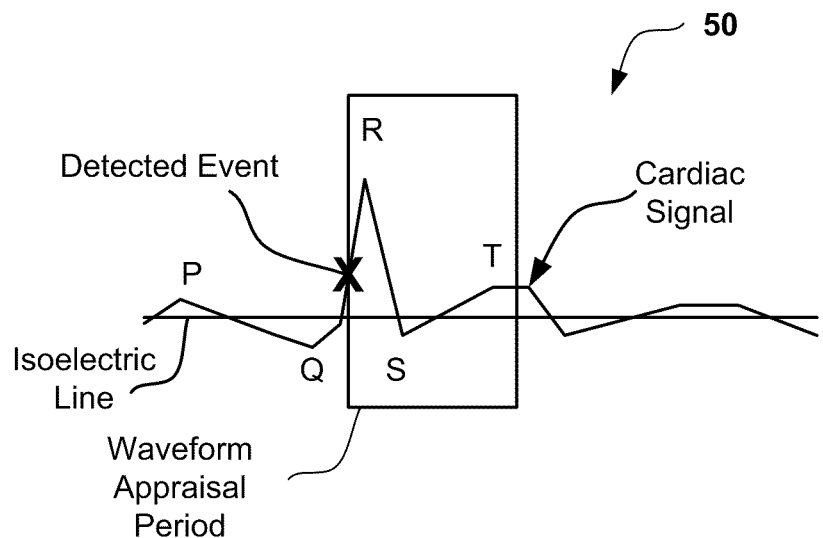
FIGS. 2 and 3 illustrate signal shapes for an example cardiac signal and an example noise signal.
Figure 3:
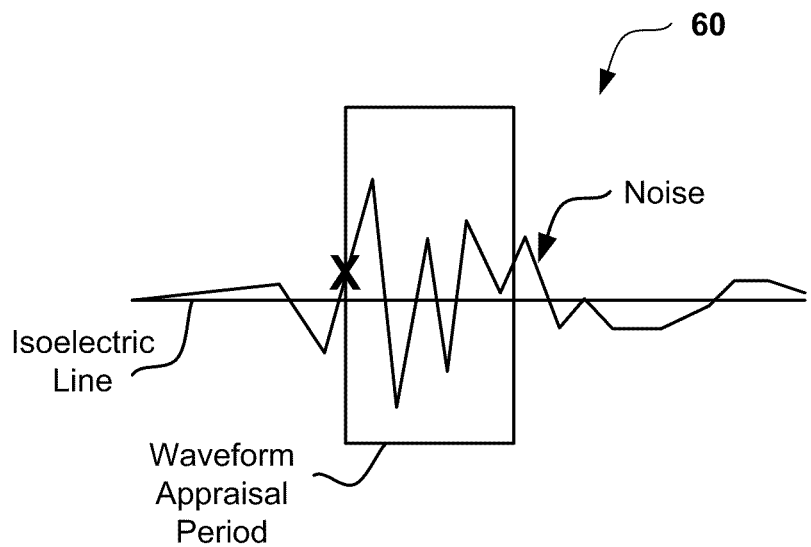

FIGS. 2 and 3 illustrate signal shapes for an example cardiac signal and an example noise signal. In FIG. 2, as shown at 50, a cardiac signal is shown relative to an isoelectric line with occurrence of a detected event highlighted by the X. The cardiac signal is shown with segments P, Q, R, S and T, each of which are named by well known convention. Following the detection X, a waveform appraisal analysis period begins. The waveform appraisal analysis period covers the R-wave and some trailing signal.

In FIG. 3, as shown at 60, an excursion from the isoelectric line causes a detection, shown as an X. However, the detection in FIG. 3 is caused by noise. Comparing FIG. 2 to FIG. 3, the cardiac signal is relatively slow moving and flat when compared to the noise signal. In illustrative examples, these features are used to distinguish noise from cardiac signal, particularly by focusing on the signal in the waveform appraisal analysis periods shown. In some examples, the waveform appraisal analysis periods may be coincidental with a refractory period. Refractory periods are periods during which the device will not declare a new detected event, and these are typically used to avoid declaring multiple detected events for a single biological event. For example, in a cardiac sensing system, a refractory period may be defined following a detection for a duration calculated to ensure that the R-wave or QRS complex are finished before the device can declare a new detected event. For present purposes, refractory and blanking periods are not the same; the difference is that a blanking period is a time during which the device cannot declare new detected events because circuitry is disabled, open or switched out (as may be done during and/or after stimulus delivery), while a refractory period is a time during which sensing circuitry is active, but new events are, by rule, not declared; for example, the detection threshold may be treated as infinite during refractory periods.

Figure 4:
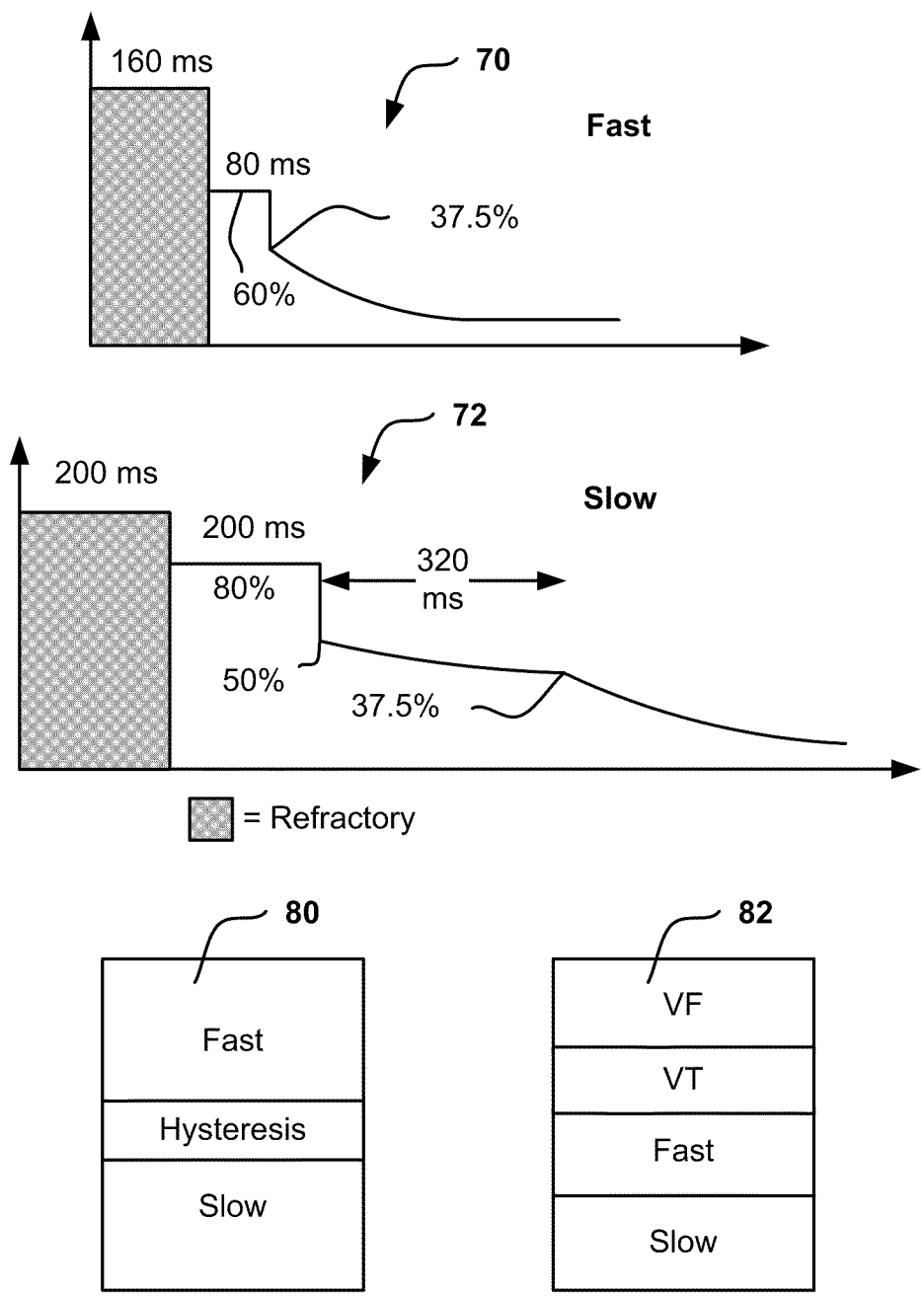
FIG. 4 shows two illustrative detection profiles and examples of how a system may select between one and the other.

FIG. 4 shows two illustrative detection profiles and examples of how a system may select between one and the other. The profiles are shown at 70 and 72. In a first profile, a refractory period (indicated by cross-hatching, as noted) extends for a period of time. Initially after refractory, a constant threshold is set as a percentage of the "estimated peak" of the detected signal. Estimated peak can be found by any suitable method; in some examples, the peak amplitude detected during the refractory period, or the peak amplitude associated with previous detected events, may be used alone, separately or averaged, for example, to calculate an estimated peak. Following the constant threshold period, which has a predetermined duration according to the detection profile, a decay period starts from another predefined percentage of the estimated peak and decays toward a detection floor.

The detection profile at 72 is shown with a refractory period again, following by a constant threshold period and two decay periods. In the illustrative example, the refractory period for profile 72 is longer than that of profile 70, and various other parameters are changed as well, including the length of the constant threshold period, the percentages used for the constant threshold and decay starting points, and the number of decay periods used. Other parameters may also change with these detection profiles 70, 72. The numbers shown for percentages and durations are merely illustrative and may vary. The overall shape of detection profiles 70, 72 merely illustrates one approach to event detection.

Labels to the right of the detection profiles 70, 72 suggest that profile 70 is for use when the detected event rate is "Fast," while profile 72 is for use when the detected rate is "Slow". This Fast/Slow usage is simply one example and is not required. One illustrative example of using rates to modify the profile is illustrated at 80. A fast zone is defined, and a slow zone is defined. Between fast and slow is a hysteresis zone, which may operate, for example, by calling the rate "Slow" until the rate crosses the lower boundary of Fast, after which it calls the rate "Fast" until the rate crosses the upper boundary of "Slow." Hysteresis prevents fast switching between the rate zones, and is optional. Another example of multiple zones is shown at 82, with zones labeled Slow, Fast, VT (for ventricular tachycardia) and VF (for ventricular fibrillation). These multiple zones may each direct different analysis in the system, or different detection profiles 70, 72. Hysteresis may or may not be provided between the several zones.

Figure 5A:
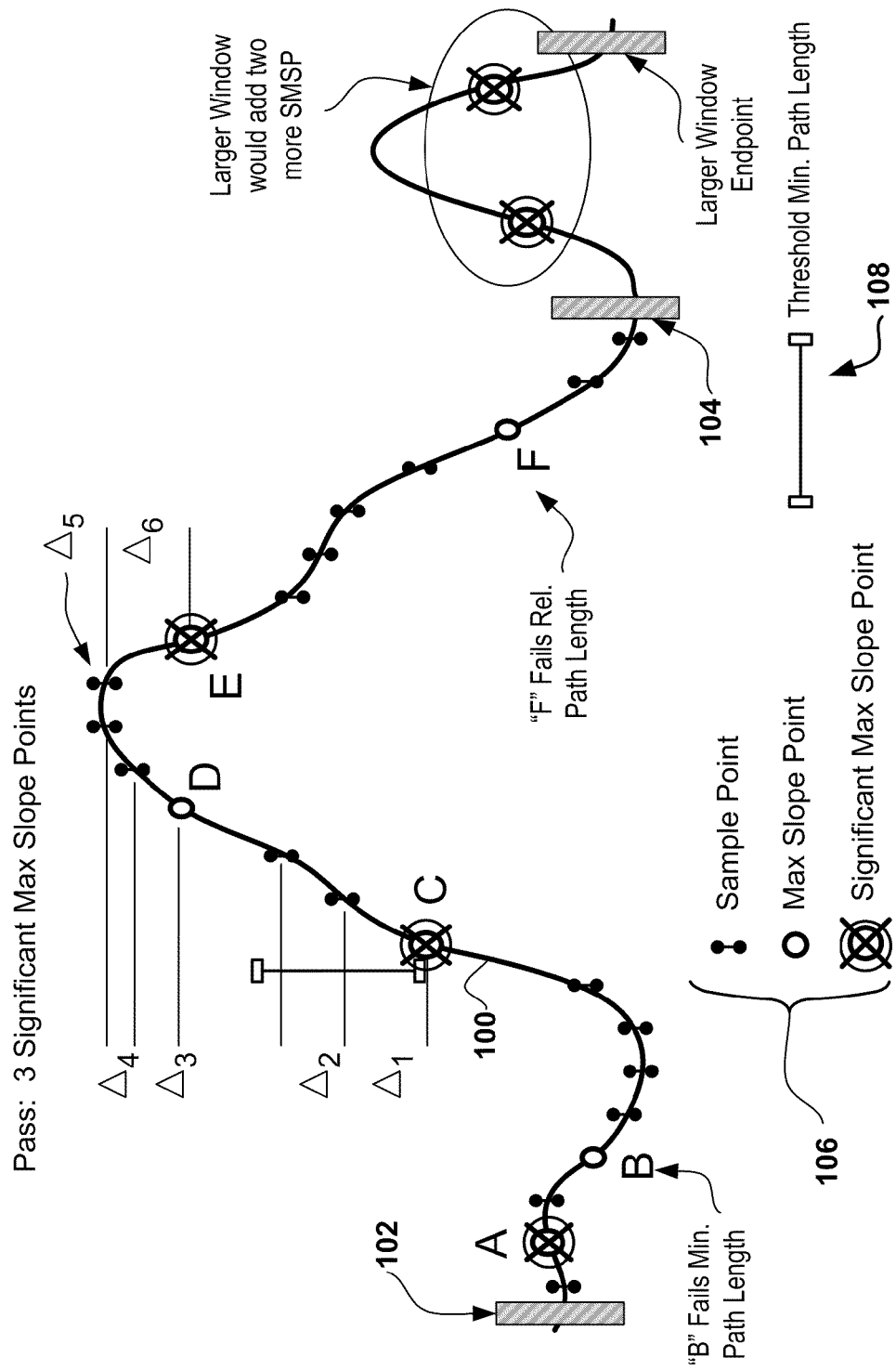
FIGS. 5A-5C graphically demonstrate illustrative approaches to waveform appraisal analysis of a detected event.
Figure 5B:
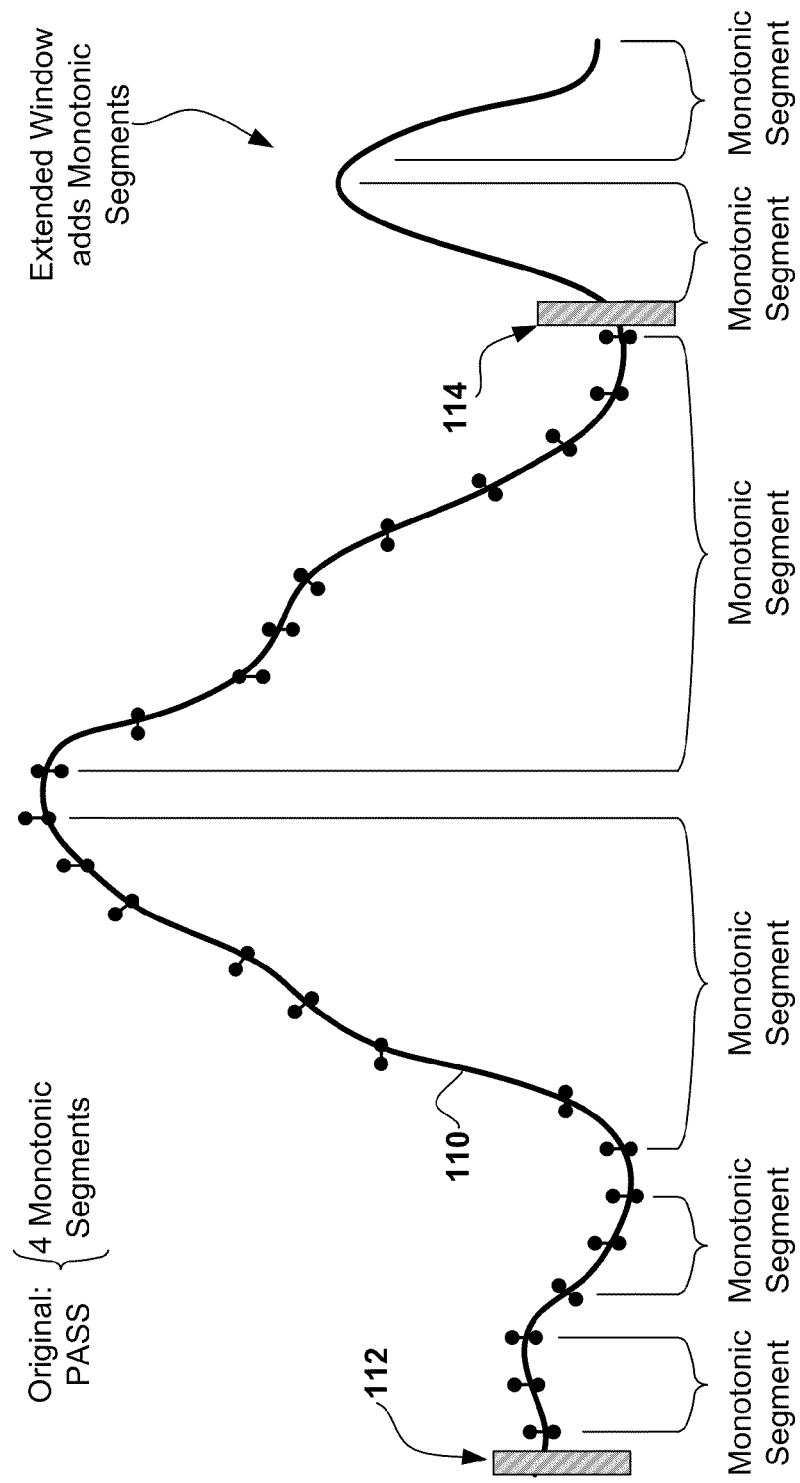
Figure 5C:
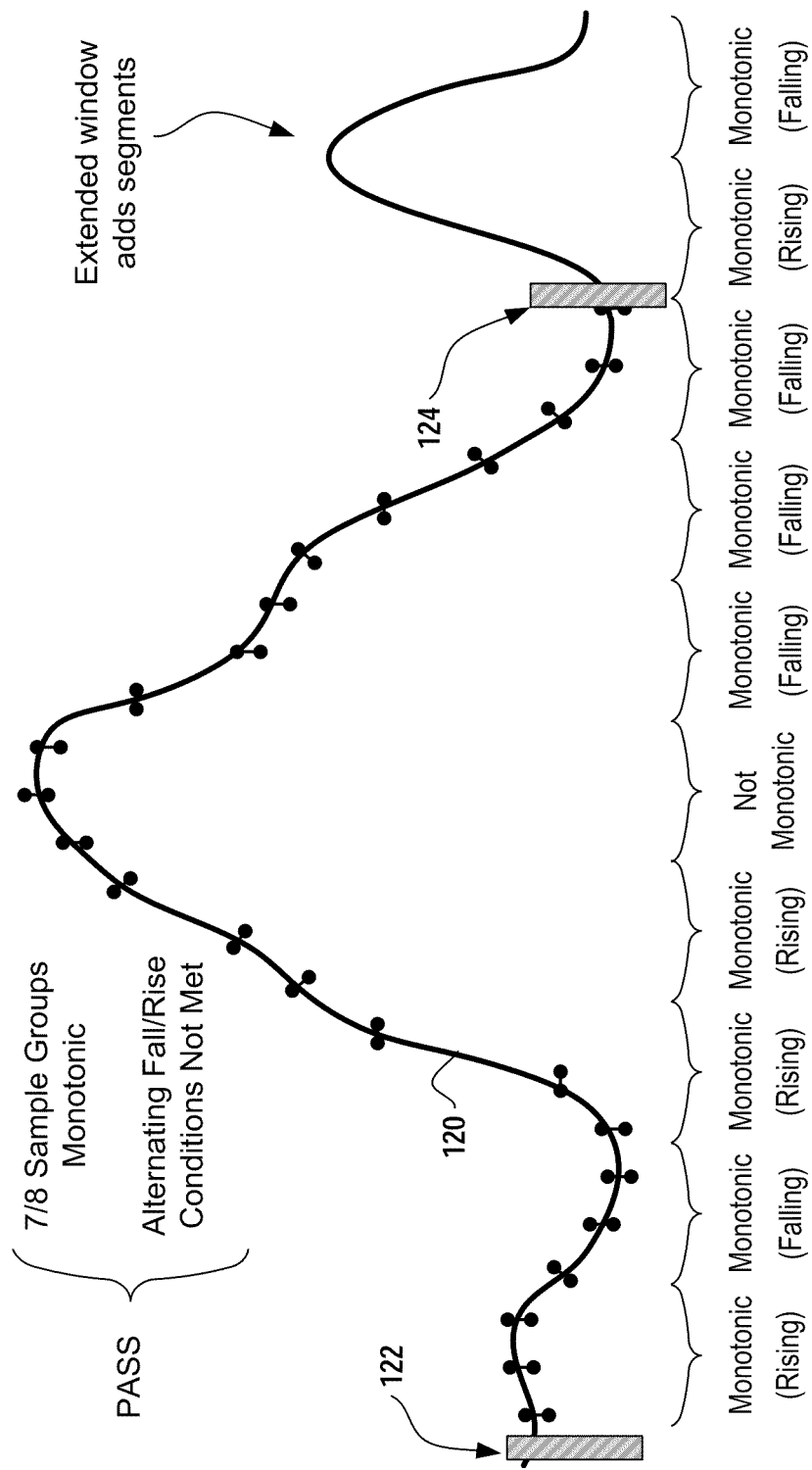

FIGS. 5A-5C graphically demonstrate illustrative approaches to waveform appraisal analysis of a detected event. In FIG. 5A, a detected event signal is shown at 100, with the analytical window beginning at 102 and ending at 104. FIG. 5A counts maximum slope points; other examples may observe different features such as zero slope points. The individual sample points are represented along the signal line 100 as double-dots, one over and one under the signal line 100, with maximum slope points shown as empty circles, and significant maximum slope points shown as circles with an X over top, as indicated at 106. The signal shown has six maximum slope points within the original window between 102 and 104, labeled A-F.

In the illustrative example, not all maximum slope points are considered "significant". In order to identify significant maximum slope points, two additional rules are applied. Both relate to "path length," which is defined for the example as a sum of the absolute value of amplitude changes between samples. The first rule calls for the path length between consecutive maximum slope points to be larger than a predetermined threshold minimum (the minimum path length rule). A minimum path length is shown for illustrative purposes at 108; the actual minimum path length can vary. The second rule calls for the path length between two maximum slope points to exceed the amplitude change between the two maximum slope points themselves (the relative path length rule).

In the analysis of FIG. 5A, the first maximum slope point is automatically treated as significant, making A the first significant maximum slope point. The next maximum slope point, B, fails the minimum path length rule as it does not change amplitude enough relative to A. The next maximum slope point, C, meets the minimum path length rule. Further, the sum of the sample-to-sample amplitude changes between A and C is larger than the actual change in amplitude from A to C, so that C meets the relative path length rule. As both rules are met, C is marked as the second significant maximum slope point.

Relative to C, D meets the minimum path length rule, but fails the relative path length rule, so D is not counted as a significant maximum slope point. From C to E, however, the minimum path length rule and the relative path length rule are both met. The path length from E to F is the same as the amplitude change from E to F, meaning that F fails the relative path length rule. No other maximum slope points fall within the window from 102 to 104. As a result, three significant maximum slope points are counted in FIG. 6A in the window from 102-104.

As can be seen on the right side of FIG. 5A, if the window is extended beyond its original endpoint at 104, a larger amount of signal data will be sensed. This may increase the number of significant maximum slope points even in a noise-free signal. Thus, the WA threshold can be adjusted to avoid over-rejecting noise-free signals by increasing the WA threshold when the window becomes larger. Alternatively, when a shorter window is identified, one would reduce the WA Threshold number for analysis as shown in FIG. 5A.

In an illustrative example, the minimum path length rule may be established by reference to the detected peak amplitude (relative to the isoelectric line) for the signal, for example, using 20-70% of the maximum peak amplitude. In another example, the minimum path length rule is set using a fixed boundary. In one embodiment, the minimum path length is about 50% of the maximum peak amplitude for the signal in the analysis period. In another embodiment, the minimum path length is about 50% of maximum peak amplitude, except that the largest minimum path length is about 20 ADC counts and the smallest minimum path length is about 10 ADC counts, when operating on a non-rectified 8-bit (256 ADC count) digital signal. Other boundaries and standards may be set, including formulas, fixed levels, and/or high and low limits, and different ADC systems may be used, or the rule may be applied in an analog signal context.

The method of FIG. 5A applies a less-than standard in which the number of significant maximum slope points is counted and if the number is less than an applied threshold, then the detection passes waveform appraisal. If there are more significant maximum slope points than the applied threshold, the detection will be identified by waveform appraisal as a suspect event.

Turning to FIG. 5B, an example is shown in which the number of monotonic segments in the signal are counted. Monotonic segments are defined as those in which the slope remains either positive or negative across the entire segment. Whenever the sample-to-sample slope goes from positive to negative or from negative to positive, a new monotonic segment begins. In this example, as with FIG. 5A, if there are more than a threshold number of monotonic segments appearing in the analysis window, the signal is considered noisy and suspect.

The signal 110 is shown with original start point 112 and original end point 114 between which four monotonic segments are counted. In the example, this signal would pass, using N=5 as the WA threshold, where having less monotonic segments than the WA threshold counts as passing. Adding a longer window, however, increases the number of monotonic segments to six, as can be seen. Given the longer window, the illustrative example increases the WA threshold to N=7, meaning that the signal still passes.

FIG. 5C shows another example. In FIG. 5C, the signal 120 is broken into sample groups which are analyzed to determine whether each sample group is monotonic or not. As opposed to FIGS. 5A and 5B, a minimum number of the threshold groups are expected to be monotonic in order to pass. As a result, a "greater than" or "greater than or equal to" rule is applied. As long as more than 6 of the 8 segments in the original window from start 122 to end 124 are monotonic, the signal is considered passing. When the window is extended, additional segments can be analyzed. Therefore, the applied rule is adjusted to call for at least 7 of the 10 segments in the longer window to be monotonic in order to pass. It should be noted that three-sample segments are considered in FIG. 5C; if desired, longer segments may be used instead. Different window sizes and settings for the number or proportion of monotonic groups may be selected.

While the sensing/event detection combination shown in FIG. 1 suggests a system that performs waveform appraisal synchronous to detected events, in other embodiments, asynchronous analysis make take place instead, for example by looking a predefined blocks of time. One example may look at one-second blocks of time, rather than relying on a refractory period duration or a duration tied to a detected event, as the example of FIG. 4 suggests. For such an example, when rates are higher, the predefined block of time may be modified. For example, when slow rates are identified, one-second blocks of time may be analyzed by waveform appraisal, and when high rates are identified, 250-millisecond blocks of time may instead by analyzed. When the block duration changes, other parameters can then be changed as well.

Referring now back to FIG. 1, one of the changes that can occur in waveform appraisal is a change in the quantity of characteristic features that will trigger identification of a suspect event. For example, with a longer analysis period (whether defined as the duration of a refractory period of detection profiles 70, 72, defined independent of refractory periods for each detected event, or defined asynchronous to event detection) may use a different threshold than a shorter analysis period. Some illustrative examples follow, using "N" as the threshold quantity of characteristic features.

In an example using significant slope points (FIG. 5A), if an about 140 millisecond analysis window is used with N=7, a threshold of N=5 would be used if the window is shortened to about 100 milliseconds, and a threshold of N=9 would be used if the window is extended to about 180 milliseconds. In another illustrative example using significant slope points (FIG. 5A), the threshold for characteristic features is set to N=6 for an analysis period of about 200 milliseconds and N=5 for an analysis period of about 160 milliseconds. For this latter example, the detection profiles of FIG. 4 may be used, the refractory periods also defining the analysis periods for waveform appraisal. As noted, refractory and waveform appraisal periods can be independent of each other instead.

Other thresholds and analysis period lengths may be used instead. For example, in some embodiments the threshold number can be set using a formula based on one or more factors. For example, the following formula may be used:

$$N = \text{INT}\left[\frac{\text{Duration}}{33}\right]$$

Where Duration stands for the duration of the period of analysis (which may be the refractory period) given in milliseconds, and INT indicates that the nearest integer value is used. The value 33 in the formula is merely illustrative, and other values may be used. The system could then use a continuously variable analysis period having a range of, for example, about 50 to about 300 milliseconds. In some examples, the Refractory period and the analysis period for waveform appraisal are the same. In other examples, these periods may be independent of one another, or may be related but not the same. In some examples, the analysis period for waveform appraisal starts at the moment of threshold crossing leading to a detected event. However, in other examples, the analysis period for waveform appraisal can begin before or after the moment of the threshold crossing that leads to a detected event.

In another illustrative example, the WA threshold may vary in response to changes in other parameters of the sensing system, as indicated at 20 in FIG. 1. A system may be designed to modify signal filtering in response to detected characteristics. For example, a filter characteristic may be varied, and the WA threshold can be changed in response; in one embodiment, reduced filter attenuation can be accompanied by changing the WA threshold to make it less aggressive as a noise identifier (that is, less likely to mark detected events as suspect) and, conversely, additional filter attenuation can be accompanied by a change in the WA threshold designed to make it more aggressive (that is, more likely to mark detected events as suspect). Alternatively, increased filter attenuation may be accompanied by changing the WA threshold to make it less aggressive, while reduced filter attenuation is accompanied by changing the WA threshold to make is more aggressive. In some examples, the WA threshold may change in response to a vector change. For example, one sensing vector may be considered characteristically more likely to encounter more biphasic signals or more complex desired signals than another sensing vector; in an illustrative embodiment, a switch from a near field vector to a far field vector is associated with a change in the WA threshold to make it less aggressive. In some examples, gain of signal amplification can be a sensing parameter that, if changed, leads to a WA threshold change; in an illustrative embodiment, an increase in gain is accompanied by changing the WA threshold to be less aggressive as the effective amplifier bandwidth decreases in keeping with the overall gain-bandwidth product.

In some examples, characteristics of the sensed signal may be triggers for changes to the WA threshold. For example, if observed QRS peaks are lower in amplitude, the reduced amplitude can be used to trigger a change in the WA threshold to reduce the likelihood of events being marked as suspect, since a lower amplitude signal resides closer to the noise floor of a system and may therefore demonstrate a lower signal-to-noise ratio even when accurately detecting the cardiac signal. In some examples, time series pattern identification can be used to identify likely noise issues across multiple detected events and, if so, the WA threshold may be change to encourage early rejection of noise by waveform appraisal, rather than relying on overdetection algorithms. In another example, identification of one or more nonsustained malignant arrhythmias (where a malignant arrhythmia is identified by the ICSD but terminates before therapy can be delivered and goes untreated) can be used as a trigger to change the WA threshold to more aggressively remove noisy detections. In another illustrative example, sensed signals may be analyzed to identify changes in posture or activity level and, in response to such changes, the WA threshold may be modified.

In another example, a factor outside of the sensing parameters or the signal analyzed by waveform appraisal can be used to modify the WA threshold. For example, an accelerometer or other sensor may be used to monitor activity level or posture, and the WA threshold may be changed to accommodate likely changes to noise or the desired signal that are expected to result from such activity level or posture. Changes to the WA threshold may also occur in response to identification of a known source of noise or basis for additional signal complexity such as, for example, activation of a concomitant implanted system (i.e., for a subcutaneous defibrillator, activation of pacing or a left ventricular assist device, or activation of a non-cardiac device such as a neurostimulator, implanted insulin or drug pump, for example), or activation of an output such as a telemetry circuit or, if the system has multiple output features, if pharmacological output is activated while electrical sensing is ongoing. In yet another example, the WA threshold may be changed in response to identification of a likely failure, such as a lead fracture, which can create sensing difficulties, where the failure such as lead fracture may be identified through analysis of the sensed signal or may be identified by analysis of other signals, or by a combination thereof.

In yet another example, the WA threshold may be configured as a learning noise detector. When a pattern of beats, or shape of waveform, or other input variable, is identified, the WA threshold may change to become more or less aggressive in identifying noise. For example, a patient receiving an implantable device may work in an environment having certain noise producing elements such as industrial equipment that creates electromagnetic interference (examples include power production/conversion equipment, arc welders or even high power transmission lines), which may have a characteristic signature that can be identified by the implanted system. If such a source of EMI is identified, the WA threshold may be modified to more aggressively identify more detections as suspect. Alternatively, if such a source of EMI is identified, filtering characteristics of the system can change and the WA threshold may be modified to become more or less aggressive. The learning process may be entirely internal to the implanted system or, alternatively, the implanted system may be programmed to identify a particular source of EMI and modify WA and/or filtering characteristics during interaction with an external programming device, for example. In one example, a characteristic pattern of a source of EMI is identified during a programming session by observing signal characteristics during a stored episode, and rules can be set for identifying recurrence of the characteristic pattern of the EMI source, with the WA threshold being changed in response to the identification of the pattern. Non-implantable systems may integrate such a detector as well.

In another illustrative embodiment, the WA threshold is calculated on a running basis in response to a continually varying analysis window. In this embodiment, the width of the analysis window is defined on a detection-to-detection basis by observing signal characteristics of each detection. For example, individual signal samples can be observed to determine whether a selected number of samples fall within a threshold amplitude of the isoelectric line. In an illustration, if the isoelectric line is zero on an analog-to-digital conversion scale going up to 128, then the end of the analysis window that starts at a detection may be defined to occur when three consecutive samples are all less than five units. This would indicate an end of the detected event. If desired, a minimum duration and/or a maximum duration for the detected event may be defined, and different relative levels and/or characteristics may be used to define the "end" of the analysis window for a detected event. Once the dynamically extended analysis window is determined for a given detected event, the WA Threshold can be calculated, and the waveform analysis technique can be performed.

Figure 6:
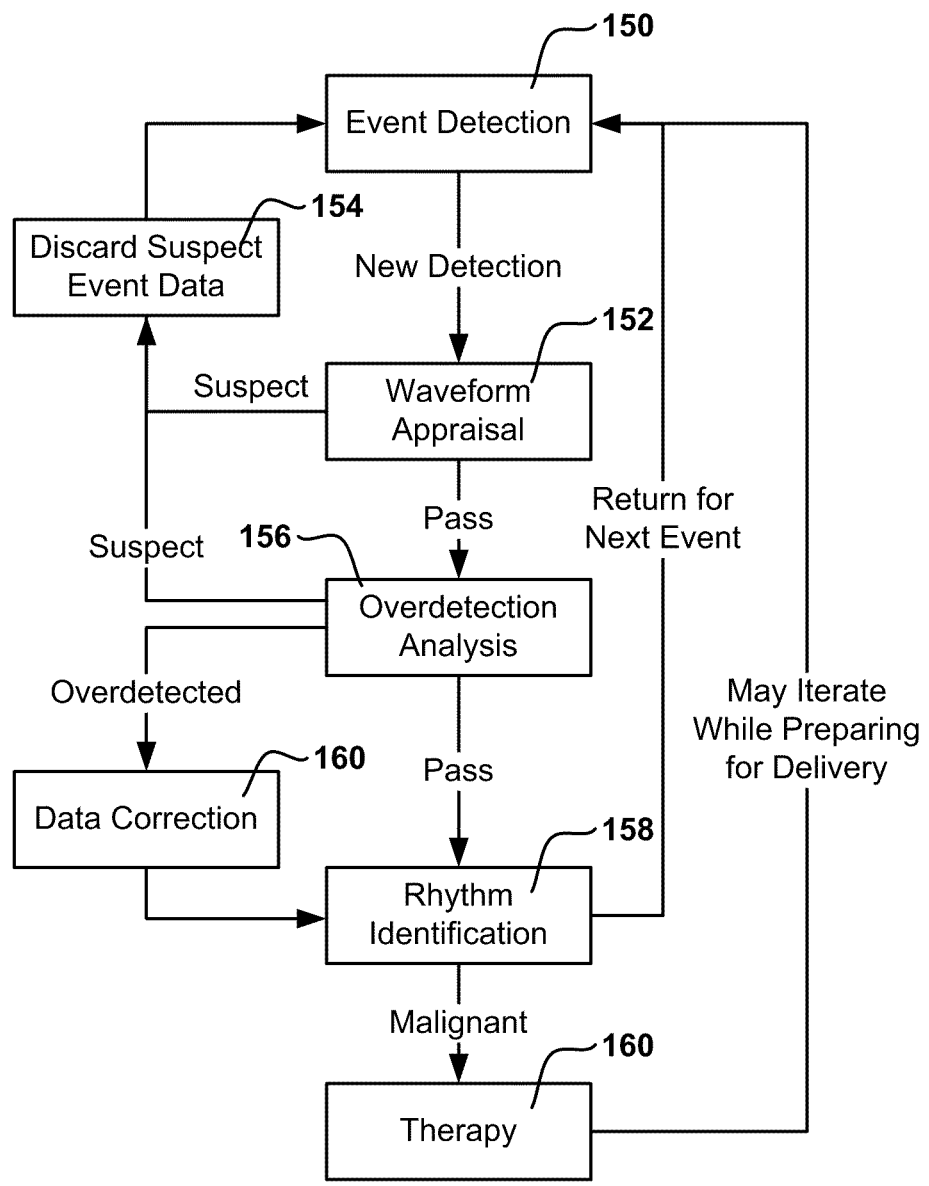
FIG. 6 shows, in block form, an illustrative example detailing the use of modifications to waveform appraisal threshold in view of detection profile settings.

FIG. 6 shows, in block form, an illustrative example integrating the above modifications to waveform appraisal into a larger method. An event-driven method is shown, with the overall loop beginning at event detection 150. Some illustrative examples of event detection appear in U.S. patent application Ser. No. 12/399,901, titled ACCURATE CARDIAC EVENT DETECTION IN AN IMPLANTABLE CARDIAC STIMULUS DEVICE, the disclosure of which is incorporated herein by reference. The terms detection and detected event can be used interchangeably herein. When a new detection is identified, waveform appraisal is performed, as shown at 152. The waveform appraisal can be dynamic, as set forth above. If waveform appraisal 152 finds a detection is suspect, it marks suspect event data as shown at 154 and the method returns to event detection 150.

If waveform appraisal 152 does not find a suspect event, the method passes to overdetection analysis 156. Overdetection analysis 156 is designed to determine whether event detection 150 has identified more than one detection for a single biological event. For example, overdetection analysis 156 may be tailored to identify instances where event detection declares two detected events for a single heart beat. Overdetection analysis 156 may find that a biological event has been overdetected, leading to data correction 160 or, alternatively, overdetection analysis 156 may determine that a detected event, when placed in the context of other detected events, appears suspect but lacks sufficient certainty to lead to data correction 160, in which case overdetection analysis 156 may optionally mark an event suspect, leading to discarding of suspect event data 154. Overdetection analysis 156 may not find an overdetection at all for example if event detection is accurate. Some illustrative examples of overdetection analysis 156 appear in U.S. patent application Ser. No. 12/399,914, issued as U.S. Pat. No. 8,160,686, titled METHODS AND DEVICES FOR ACCURATELY CLASSIFYING CARDIAC ACTIVITY, filed Mar. 6, 2009, and U.S. patent application Ser. No. 12/437,547, issued as U.S. Pat. No. 8,160,687, titled METHODS AND DEVICES FOR ACCURATELY CLASSIFYING CARDIAC ACTIVITY, filed May 7, 2009, U.S. patent application Ser. No. 12/913,642, issued as U.S. Pat. No. 8,265,737, filed on even date herewith and which claims the benefit of U.S. Provisional Patent Application No. 61/255,249, both titled METHODS AND DEVICES FOR IDENTIFYING OVERDETECTION OF CARDIAC SIGNALS, the disclosures of which are incorporated herein by reference.

Following overdetection analysis 156 and/or data correction 160, the method continues with rhythm identification 158, where analysis of the overall rhythm and its possible need for therapy is performed. Illustrative examples of this analysis appear in U.S. Pat. No. 6,754,528, titled APPARATUS AND METHOD OF ARRHYTHMIA DETECTION IN A SUBCUTANEOUS IMPLANTABLE CARDIOVERTER/ DEFIBRILLATOR, U.S. Pat. No. 7,330,757, titled METHOD FOR DISCRIMINATING BETWEEN VENTRICULAR AND SUPRAVENTRICULAR ARRHYTHMIAS, U.S. patent application Ser. No. 12/399,914, now issued as U.S. Pat. No. 8,160,686, titled METHODS AND DEVICES FOR ACCURATELY CLASSIFYING CARDIAC ACTIVITY, U.S. patent application Ser. No. 12/437,547, now issued as U.S. Pat. No. 8,160,687, titled METHODS AND DEVICES FOR ACCURATELY CLASSIFYING CARDIAC ACTIVITY, U.S. patent application Ser. No. 12/826,241, titled ADAPTIVE CONFIRMATION OF TREATABLE ARRHYTHMIA IN IMPLANTABLE CARDIAC STIMULUS DEVICES, which claims the benefit of U.S. Provisional Patent Application No. 61/221,316, titled CONFIRMATION OF TREATABLE ARRHYTHMIA IN IMPLANTABLE CARDIAC STIMULUS DEVICES, and U.S. patent application Ser. No. 11/042,911, titled METHOD FOR ADAPTING CHARGE INITIATION FOR AN IMPLANTABLE CARDIOVERTER-DEFIBRILLATOR, now U.S. Patent Application Publication Number 2006-0167503, also issued as U.S. Pat. No. 8,160,697, the disclosures of which are incorporated herein by reference.

If rhythm identification 158 identifies a treatable condition, then therapy delivery block 160 can be called. Any suitable type of therapy can be delivered including, for example and without limitation, defibrillation, cardioversion, anti-tachycardia pacing, bradycardia pacing, or any other suitable therapies. Non-electrical therapy may be delivered, such as pharmaceutical delivery. For some systems, the method may iterate while preparations for therapy delivery take place.

Figure 7:
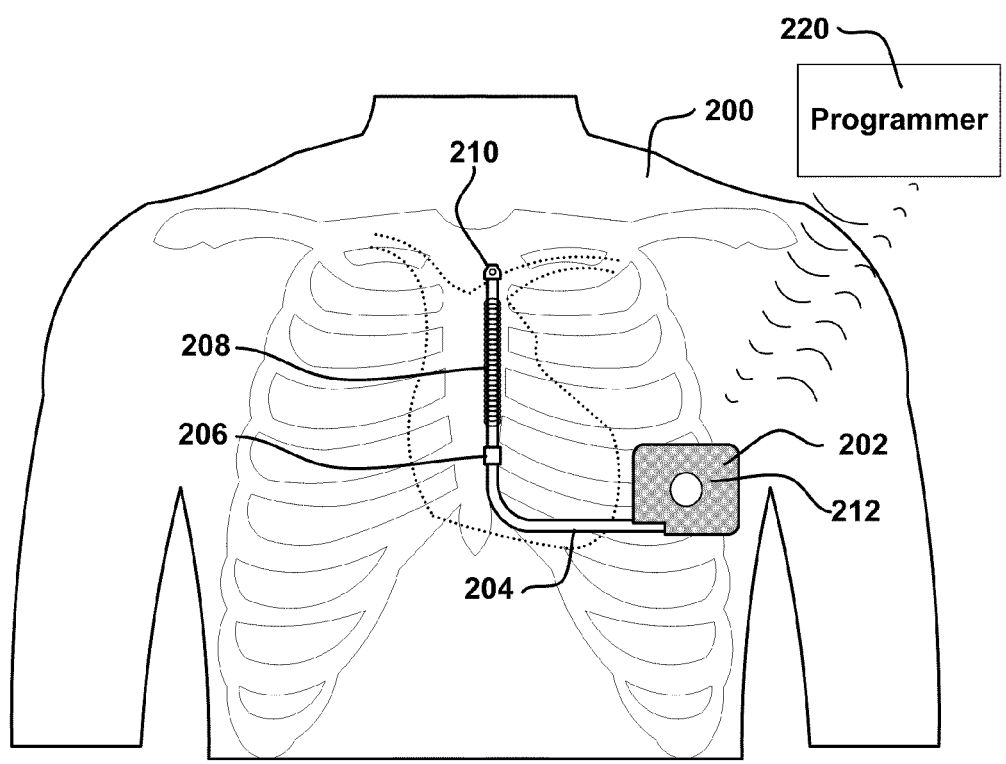
FIG. 7 shows an illustrative implantable cardiac stimulus system relative to a patient's heart.

FIG. 7 shows an illustrative implantable medical device and implant location. More particularly, an illustrative subcutaneous-only ICSD system is shown in FIG. 7. The system is shown relative to a patient 200, and includes a canister 202 coupled to a lead 204. The canister 202 preferably houses operational circuitry for performing analysis of cardiac activity and for providing a therapy output. The operational circuitry may include batteries, input/output circuitry, power capacitor(s), high voltage charging circuit(s), logic circuits, controller(s), memory, communication components, etc., as known in the art. Some examples use a microcontroller. For example, output circuitry may include a capacitor that can be charged for therapy delivery and high voltage switches for controlling output delivery.

Electrodes are disposed at locations throughout the system including, for example, an electrode 212 on the canister 202, and electrodes 206, 208 and 210 on lead 204. The electrodes 206, 208, 210, 212 may take any suitable form and can be made of any suitable material. For example, the canister electrode 212 may be an isolated button electrode or it may be a region or surface of the canister 202, and the electrodes 206, 208, 210 on lead 204 may be coil electrodes, ring electrodes, or other structures known in the art. More or fewer electrodes may be provided. The lead 204 may be designed as shown in U.S. Provisional Patent Application No. 61/122,327, titled IMPLANTABLE DEFIBRILLATOR SYSTEMS AND METHODS WITH MITIGATIONS FOR SATURATION AVOIDANCE AND ACCOMMODATION, the disclosure of which is incorporated herein by reference. Other lead designs may be used as well.

Examples of sensing vector analysis and selection using electrodes 206, 208, 210, and/or 212 are shown, for example, in U.S. Patent Application Publication Number 2007-0276445 titled SYSTEMS AND METHODS FOR SENSING VECTOR SELECTION IN AN IMPLANTABLE MEDICAL DEVICE. Other uses of multiple vectors are shown, for example, in U.S. Pat. No. 7,392,085 titled MULTIPLE ELECTRODE VECTORS FOR IMPLANTABLE CARDIAC TREATMENT DEVICES. Another embodiment considers posture in vector analysis, for example, as discussed in U.S. Patent Application Publication Number 2008-0188901, now issued as U.S. Pat. No. 8,200,341, titled SENSING VECTOR SELECTION IN A CARDIAC STIMULUS DEVICE WITH POSTURAL ASSESSMENT. The disclosures of these patents and applications are each incorporated herein by reference. Rather than selecting a single vector for default use, multiple sensing vectors may be analyzed, sequentially or in combination.

Therapy may be applied using any chosen pair of electrodes. An illustrative example uses the can electrode 212 and the coil electrode 208 to apply therapy. Other electrode combinations may be used. Therapy may include mono-, bi- or other multi-phasic waveforms. Ranges for therapy delivery energy may include, for example, ranges from 0.1 Joules to 35 or more Joules for transvenous and/or epicardial systems, and sometimes higher ranges for subcutaneous therapy delivery, for example, 0.1 Joules up to or in excess of 40, 65, 80 or 100 Joules. Therapy may also be provided in the forms of cardioversion or antitachycardia pacing (ATP). Therapy may be delivered in a tiered sequence from lesser to greater amplitude (such as ATP first and defibrillation if ATP fails) and/or therapy may be delivered depending upon the rate of arrhythmia (such as ATP for rates indicating tachycardia and defibrillation for rates indicating fibrillation). Therapy may take the form of bradycardia pacing.

FIG. 7 omits several anatomical landmarks. The illustrative system shown may be implanted beneath the skin outside of the ribcage of the implantee. The location illustratively shown would place the canister 202 at approximately the left axilla of the implantee, level with the cardiac apex, with the lead 204 extending medially toward the xiphoid and then toward the head of the implantee along the left side of the sternum. One illustrative example uses a method/system as shown in commonly assigned U.S. Patent Application Publication Number 2006-0122676, now issued as U.S. Pat. No. 7,655,014, entitled APPARATUS AND METHOD FOR SUBCUTANEOUS ELECTRODE INSERTION, the disclosure of which is incorporated herein by reference. Other illustrative subcutaneous systems and locations are shown in commonly assigned U.S. Pat. Nos. 6,647,292, 6,721,597 and 7,149,575, and the disclosures of each of these are incorporated herein by reference.

The present invention may be embodied in cardiac systems having various implant configurations including, for example, other subcutaneous-only, vascular-only, and/or transvenous implantation configurations/locations. The system or its electrodes may be placed in epicardial locations. The canister 202 may be placed in anterior, lateral, and/or posterior positions including, without limitation, axillary, sub-clavicular, pectoral, and sub-pectoral positions, as well as the left or right side of the implantee's torso and/or in the abdomen. Intravascular implantation of an ICSD has also been proposed. The lead 204 may be placed in any of a number of suitable configurations including anterior-posterior subcutaneous, anterior-only subcutaneous, having one or more transvenous or other vascular electrodes, and or using epicardial electrodes. Multiple leads 204 may be used as well. A unitary system may omit lead 204 and instead include all electrodes on the canister 202, which may be flexible, malleable and/or shaped for ease of implantation and wearability.

The present invention is not intended to be limited to any particular hardware, implant location or configuration. Instead, it is intended for use in any implantable cardiac therapy system. Some embodiments may include monitoring systems. For example, monitoring functions such as annunciation or data storage may be manipulated, rather than controlling therapy delivery, in response to detected event analysis. A monitoring system may be used for diagnostic purposes (such as to identify the cause of syncope) or it may be used to demonstrate the suitability of analytical methods or implantable systems for a particular patient.

Some examples can associate with an external programmer 220 configured to communicate with an implanted device for various purposes, including, for example and without limitation, one or more of the following: device testing; upload new/revised software; modify sensing, detection or therapy settings; determine the status or history of device operation, battery life, or lead integrity; and/or download data relating to the device or implantee's condition, prior data capture, or treatment. Any suitable communication method or system may be used, such as various protocols and hardware widely known in the art including, for example, MICS, inductive telemetry, RF telemetry, Bluetooth, etc.

Many of the examples provided above focus on the use of an implantable device to observe cardiac activity. In additional embodiments, an implantable device can be used to analyze signals coming from any predetermined origin, including the nervous system parameters, lung/diaphragm activity, digestive activity, for example. In some embodiments, particular chambers of the heart or other organ are analyzed, for example with near field sensing configurations adapted for the atria or ventricles of the heart or even a single one of these chambers, such as the left atrium. Across such examples, different threshold pairs may be provided with different refractory or analysis window durations for use in different configurations or implant locations. For example, using significant maximum slope points as characteristic features (see FIG. 5A, above):

a: in a subcutaneous defibrillator, a first analysis window in the range of about 140-170 milliseconds with a threshold of 5 characteristic features, and a second analysis window in the range of about 180-220 milliseconds with a threshold of 6 characteristic features;

b: in a transvenous cardiac sensing, pacing and/or defibrillation system, a first analysis window of about 120-160 milliseconds with a threshold of 7 characteristic features and a second analysis window of about 80-110 milliseconds with a threshold of 5 characteristic features;

c: in another example, a first analysis window of about 100-130 milliseconds with a threshold of 5 characteristic features, and a second analysis window of about 140-170 milliseconds with a threshold of 6 characteristic features, and a third analysis window of about 180-220 milliseconds with a threshold of 8 characteristic features; and d: in another example, a first window having shorter duration is used for a first sensing electrode pair operating in the near field (for example, between two intraventricular electrodes), a second window having longer duration is used for a second sensing electrode pair operating in the transvenous far field (for example, a first electrode in a ventricle and a second electrode on an infraclavicular housing), and a third window having a subcutaneous far field signal (first and second subcutaneous electrodes), with different characteristic feature thresholds applied for each window and location.

Other window sizes, characteristic feature numbers and implant location/sensing electrode pairings can be used.

Several embodiments disclosed herein are shown as devices; the present invention also includes methods of operating, implanting and using such device embodiments. Likewise, for embodiments disclosed as methods, devices configured for the performance of such methods comprise additional embodiments.

Those skilled in the art will recognize that the present invention may be manifested in a variety of forms other than the specific embodiments described and contemplated herein. Accordingly, departures in form and detail may be made without departing from the scope and spirit of the present invention.

What is claimed is:

1. An implantable device (ID) comprising operational circuitry and a plurality of electrodes coupled to the operational circuitry to allow observation of electrical activity by the operational circuitry when the ID is implanted in a patient, wherein the operational circuitry is configured to perform a method of detecting signals comprising:
   sensing electrical activity using the electrodes;
   detecting a detected event in the electrical activity;
   analyzing the detected event by defining an analysis window having an analysis window duration, identifying characteristic features of the electrical activity sensed during the analysis window, and counting the characteristic features that occur during the analysis window to generate a characteristic feature count for the detected event; and
   comparing the characteristic feature count to a predefined threshold and either rejecting the detected event as suspect or accepting the detected event as likely being of predetermined origin;
   wherein the operational circuitry is further configured to identify a change in a sensing parameter of the system and modify the predefined threshold to account for the changed sensing parameter.

2. The ID of claim 1 wherein the operational circuitry is configured to identify a change in filtering characteristics as a change in a sensing parameter and to modify the predefined threshold.

3. The ID of claim 2 wherein the operational circuitry is configured to change the filtering characteristics and modify the predefined threshold as follows:
   while in a first mode, applying greater attenuation to one or more frequencies and setting the predefined threshold at a first level; and
   while in a second mode, applying lesser attenuation to the one or more frequencies and setting the predefined threshold at a second level.

4. The ID of claim 1 wherein:
   the plurality of electrodes comprises at least three electrodes;
   the operational circuitry is configured to select subsets of the at least three electrodes such that at least first and second sensing vectors are defined; and
   the recited change in a sensing parameter comprises changing from use of the first sensing vector to use of the second sensing vector.

5. The ID of claim 1 wherein:
   the operational circuitry comprises input amplifier circuitry for receiving signal from the electrodes, the input amplifier circuitry having a selectable gain; and
   the recited change in a sensing parameter comprises change in the gain of the input amplifier circuitry of the operational circuitry.

6. An implantable device (ID) comprising operational circuitry and a plurality of electrodes coupled to the operational circuitry to allow observation of electrical activity by the operational circuitry when the ID is implanted in a patient, wherein the operational circuitry is configured to perform a method of detecting signals comprising:
   sensing electrical activity using the electrodes;
   detecting a detected event in the electrical activity;
   analyzing the detected event by defining an analysis window having an analysis window duration, identifying characteristic features of the electrical activity sensed during the analysis window, and counting the characteristic features that occur during the analysis window to generate a characteristic feature count for the detected event; and
   comparing the characteristic feature count to a predefined threshold and either rejecting the detected event as suspect or accepting the detected event as likely being of predetermined origin;
   wherein the operational circuitry is further configured to identify a modification to a sensing characteristic and modify the predefined threshold to account for the sensing characteristic.

7. The ID of claim 6 wherein the sensing characteristic comprises a pattern in the sensed electrical signal indicative of a predetermined source of noise.

8. The ID of claim 6 wherein:
   the operational circuitry is configured to send and receive signals from another, separate device in a communication session; and
   the sensing characteristic includes a determination that the ID and the separate device have initiated a communication session.

9. The ID of claim 6 wherein:
   the operational circuitry is configured to send and receive signals from another, separate device in a communication session;
   the operational circuitry is configured to identify an activation message from the separate device indicating that the separate device is or will activate an output that may interfere with sensing; and
   the sensing characteristic includes a determination that an activation message has been received from the separate device.

10. The ID of claim 6 wherein:
    the operational circuitry comprises a position sensor for identifying a posture or position of the patient; and
    the sensing characteristic comprises an output of the position sensor indicating a predetermined posture or position.

11. The ID of claim 6 wherein:
    the operational circuitry comprises an activity sensor for characterizing a level of activity of the patient; and
    the sensing characteristic comprises an output of the activity sensor indicating a predetermined level of activity.

12. The ID of claim 6 wherein the operational circuitry is configured to identify a non-sustained treatable event, and wherein the sensing characteristic is a non-sustained treatable event.

13. The ID of claim 6 wherein the operational circuitry is configured to identify a change in filtering characteristics as the sensing characteristic.

14. The ID of claim 6 wherein:
    the plurality of electrodes comprises at least three electrodes;
    the operational circuitry is configured to select subsets of the at least three electrodes such that at least first and second sensing vectors are defined; and
    the sensing characteristic comprises a change from use of the first sensing vector to use of the second sensing vector by the operational circuitry.

15. The ID of claim 6 wherein:
    the operational circuitry comprises input amplifier circuitry for receiving signal from the electrodes, the input amplifier circuitry having a selectable gain; and
    the sensing characteristic comprises a change in the gain of the input amplifier circuitry of the operational circuitry.

16. A method of operation in an implantable device (ID) comprising operational circuitry and a plurality of electrodes coupled to the operational circuitry to allow observation of electrical activity by the operational circuitry when the ID is implanted in a patient, the method comprising:

the operational circuitry sensing electrical activity using the electrodes;

the operational circuitry detecting a detected event in the electrical activity;

the operational circuitry analyzing the detected event by defining an analysis window having an analysis window duration, identifying characteristic features of the electrical activity sensed during the analysis window, and counting the characteristic features that occur during the analysis window to generate a characteristic feature count for the detected event; and the operational circuitry comparing the characteristic feature count to a predefined threshold and either rejecting the detected event as suspect or accepting the detected event as likely being of predetermined origin;

wherein the method further comprises the operational circuitry identifying a change in a sensing parameter of the system and modifying the predefined threshold to account for the changed sensing parameter.

17. The method of claim 16 further comprising the operational circuitry identifying a change in filtering characteristics as a change in a sensing parameter, and to modifying the predefined threshold in response to the change in filtering characteristics.

18. The method of claim 17 further comprising the operational circuitry changing the filtering characteristics and modifying the predefined threshold as follows:

while in a first mode, the operational circuitry applying greater attenuation to one or more frequencies and setting the predefined threshold at a first level; and while in a second mode, the operational circuitry applying lesser attenuation to the one or more frequencies and setting the predefined threshold at a second level.

19. The method of claim 16 wherein:

the plurality of electrodes comprises at least three electrodes;

the operational circuitry is configured to select subsets of the at least three electrodes such that at least first and second sensing vectors are defined; and the recited step of the operational circuitry identifying a change in a sensing parameter includes the operational circuitry changing from use of the first sensing vector to use of the second sensing vector.

20. The method of claim 16:

the operational circuitry comprises input amplifier circuitry for receiving signal from the electrodes, the input amplifier circuitry having a selectable gain; and the recited step of the operational circuitry identifying a change in a sensing parameter includes the operational circuitry changing the gain of the input amplifier circuitry of the operational circuitry.

* * * * *